United States Patent
Sato et al.

(10) Patent No.: US 6,660,183 B2
(45) Date of Patent: Dec. 9, 2003

(54) SELF-DOPED CONDUCTIVE POLYMER, MONOMER FOR SYNTHESIZING SELF-DOPED CONDUCTIVE POLYMER, AND PROCESSES OF PRODUCING THE SAME

(75) Inventors: Makoto Sato, Nishikasugai-gun (JP); Kuniyoshi Kondo, Nishikasugai-gun (JP); Hiromitsu Tanaka, Aichi-gun (JP); Arimitsu Usuki, Aichi-gun (JP)

(73) Assignee: Toyoda Gosei Co., Ltd., Aichi-ken (JP)

( * ) Notice: Subject to any disclaimer, the term of this patent is extended or adjusted under 35 U.S.C. 154(b) by 0 days.

(21) Appl. No.: 10/167,431

(22) Filed: Jun. 13, 2002

(65) Prior Publication Data

US 2003/0013912 A1 Jan. 16, 2003

(30) Foreign Application Priority Data

Jun. 15, 2001 (JP) .................................. P. 2001-182369

(51) Int. Cl.$^7$ ........................ C09K 19/58; C09K 19/06; C07C 321/00
(52) U.S. Cl. ................. 252/299.2; 528/271; 528/373; 528/391; 252/299.62; 252/299.64; 560/9; 560/11; 560/14
(58) Field of Search ................... 528/271, 373, 528/391; 252/299.2, 299.62, 299.64; 560/9, 11, 14

(56) References Cited

U.S. PATENT DOCUMENTS

| 5,064,572 A | 11/1991 | Ohnishi et al. |
| 5,604,292 A | 2/1997 | Stenger-Smith et al. |
| 5,639,398 A | 6/1997 | Rhee et al. |

FOREIGN PATENT DOCUMENTS

| JP | 8-134189 | 5/1996 |
| WO | WO 98/46652 | 10/1998 |

*Primary Examiner*—Samuel A. Acquah
(74) *Attorney, Agent, or Firm*—Posz & Bethards, PLC

(57) ABSTRACT

A process for producing an aromatic monomer for synthesizing a self-doped conductive polymer, the process comprising:
  introducing an alkoxysulfonic acid group as a self-doping group to a benzene or naphthalene derivative having a hydroxyl group bonded to an aromatic ring thereof by alkanesulfonation of the hydroxyl group;
  protecting the self-doping group by converting to an acid halide form by sulfonyl halogenation; and
  introducing two chloromethyl groups as a polymerizable groups into the aromatic ring.

9 Claims, 2 Drawing Sheets

SELF-DOPED CONDUCTIVE POLYMER, MONOMER FOR SYNTHESIZING SELF-DOPED CONDUCTIVE POLYMER, AND PROCESSES OF PRODUCING THE SAME

FIELD OF THE INVENTION

This invention relates to a monomer for synthesizing a self-doped conductive polymer, a process of producing the monomer, a self-doped conductive polymer, and a process of producing a self-doped conductive polymer.

The terminology "self-doped conductive polymer" means a polymer having a functional group serving as a dopant covalently bonded to the backbone thereof either directly or via a spacer so as to have controlled conductivity.

While the present invention will be described with particular reference to poly[(2,5-dipropoxysulfonic acid)phenylene-1,4-vinylene] as a self-doped conductive polymer (hereinafter referred to as a self-doped PPV), the present invention is not limited thereto. The present invention is applicable to synthesis of any aromatic monomer from a benzene or naphthalene derivative having a hydroxyl group bonded to its aromatic nucleus and self-doped conductive polymers obtained therefrom.

BACKGROUND OF THE INVENTION

Conductive polymers have been engaging attention for applications in the electric and electronic industries as various conductive materials or optical materials providing parts demanding high processability, such as electrodes, sensors, electronic display devices, nonlinear optical devices, and photoelectric devices, antistatic agents, automotive parts, electromagnetic shields, and the like.

Poly(phenylene vinylene)s (PPVs) have recently been of interest as conductive polymers partly because of their ease of handling. PPVs can be rendered self-doped by introducing a self-doping group thereby to enjoy improvements in conductivity, safety, and the like.

Introduction of an alkoxysulfonic acid group, one of self-doping groups, into an aromatic ring of a conductive polymer has been carried out by, for example, a process starting with an aromatic compound having a halogen directly bonded to the aromatic ring there as illustrated below.

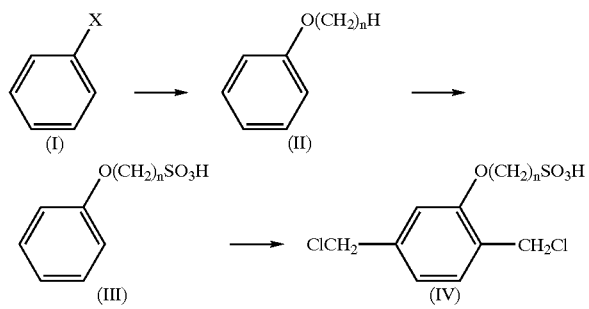

wherein n is an integer; and X is Cl or Br.

That is, a self-doping group-containing compound (III) is synthesized by once substituting the halogen atom of a compound (I) with an alkoxy group, to which a sulfonic acid group is added. The resulting compound (III) is chloromethylated to obtain a monomer (IV) having a self-doping group and a polymerizable group (chloromethyl group) which is ready to be polymerized to produce a self-doped conductive polymer.

SUMMARY OF THE INVENTION

Each step involved in the above-mentioned conventional process of producing a self-doping monomer involves difficulty in purifying the product, which has resulted in poor overall yield. In addition, the self-doping group of the monomer is apt to cause a side reaction in the polymerization reaction, tending to result in a failure to obtain a desired self-doped conductive polymer.

An object of the present invention is to provide a process for producing a self-doped conductive polymer in high yield without involving a side reaction during polymerization.

As a result of intensive investigations, the present inventors have reached the present invention.

The invention provides, in its first aspect, a process of producing a monomer for synthesizing a self-doped conductive polymer characterized by starting with a benzene or naphthalene derivative (e.g., hydroquinones and phenols) having a hydroxyl group. That is, the invention provides a process of producing a monomer for synthesizing a self-doped conductive polymer comprising introducing an alkoxysulfonic acid group as a self-doping group to a benzene or naphthalene derivative having a hydroxyl group bonded to the aromatic ring thereof by alkanesulfonation of the hydroxyl group, protecting the self-doping group by converting to an acid halide form by sulfonyl halogenation, and introducing a chloromethyl group as a polymerizable group into the aromatic ring.

It is preferred for the starting benzene or naphthalene derivative to have two hydroxyl groups for providing conductive polymers having two self-doping groups per repeating unit, which favors reaching a desired conductivity.

It is preferred for the alkanesulfonic acid used for the alkanesulfonation has a straight-chain alkane moiety containing 2 to 12 carbon atoms. With only one carbon atom in the alkane moiety, the electron attraction by the sulfonic acid moiety reduces the electron density on the conductive polymer, resulting in a reduction of conductivity. Too many carbon atoms in the alkane moiety makes the side chain too bulky to allow polymer main chains to come into contact with each other or get close to each other. As a result, electron conduction would be hindered to reduce the conductivity.

Thionyl chloride is a preferred chlorinating agent for achieving the sulfonyl halogenation with no side reactions. Other halogenating agents are useful as well unless they cause a side reaction or influence the subsequent reaction.

The invention provides, in its second aspect, a monomer for synthesizing a self-doped conductive polymer prepared by the above-described process which is represented by formula (1):

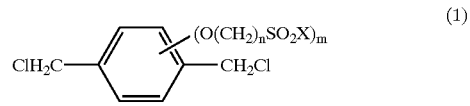

wherein m represents 1 or 2; n represents an integer of 2 to 12; and X represents chlorine or bromine.

The invention also provides, in its third aspect, a process of producing a self-doped conductive polymer by using an aromatic monomer prepared by the above-described process.

That is, the invention provides a process of producing a self-doped conductive polymer which comprises converting the chloromethyl group of the aromatic monomer into a sulfonium salt form, polycondensing the sulfonium salt monomer to form an intermediate polymer, releasing the sulfonium salt moiety from the intermediate polymer to form a phenylene vinylene backbone or a naphthylene vinylene backbone, and deprotecting the protected self-doping group by oxidation.

The invention also provides a process of producing a self-doped conductive polymer which comprises dehydrohalogenation polymerization of the aromatic monomer at the polymerizable group to form a phenylene vinylene backbone or a naphthylene vinylene backbone and deprotecting the protected self-doping group by oxidation.

The invention also provides, in its fourth aspect, a self-doped conductive polymer represented by formula (2):

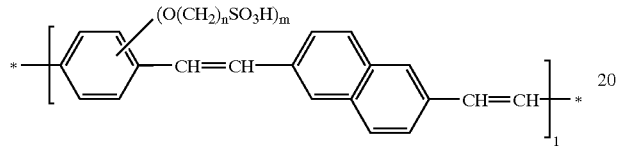

(2)

wherein 1 represents an integer of 10 to $10^4$; m represents 1 or 2; and n represents an integer of 2 to 12, which is synthesized by the above-described processes.

Having a phenylene vinylene backbone and a naphthylene vinylene backbone, the self-doped conductive polymer represented by formula (2) has a pi-electron conjugated structure and exhibits relatively satisfactory conductivity, high processability, and ease of handling.

DETAILED DESCRIPTION OF THE INVENTION

Figure 1:
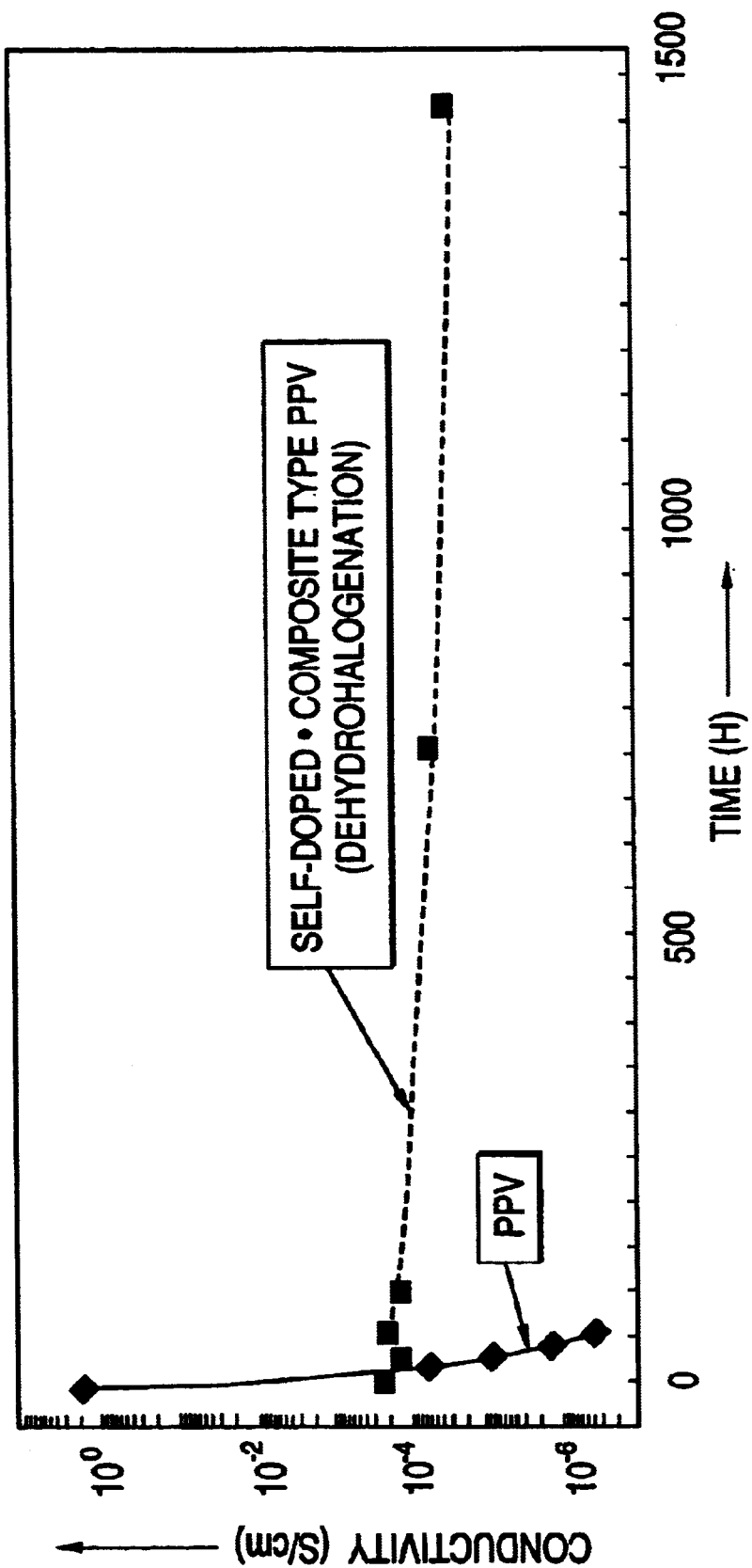
FIG. 1 is a graph showing conductivity change of conductive polymers of the present invention with time.

The present invention will be described in detail chiefly with reference to synthesis of a self-doped PPV.

Conditions for syntheses hereinafter described are subject to alteration with variation of temperature, pressure, etc. as is obvious to one skilled in the art. Therefore, it should be understood that the conditions described are no more than illustrative examples, still less limiting the present invention. Likewise, solvents and the like used here are no more than typical examples, and whatever fit for the intended purposes, such as dissolution, separation, and washing, can be used according to the purpose.

For instance, solvents can be selected from water, sulfuric acid, fuming sulfuric acid, forming acid, acetic acid, propionic acid, acetic anhydride, ethers (e.g., tetrahydrofuran, dioxane, and diethyl ether), polar solvents (e.g., dimethylformamide, acetonitrile, benzonitrile, N-methylpyrrolidone, and dimethyl sulfoxide), esters (e.g., ethyl acetate and butyl acetate), non-aromatic chlorine-containing solvents (e.g., chloroform and methylene chloride), and mixtures of two or more thereof.

An example of the synthesis of the aromatic monomer according to the invention which is capable of providing a self-doped PPV is illustrated in scheme A.

Scheme A:

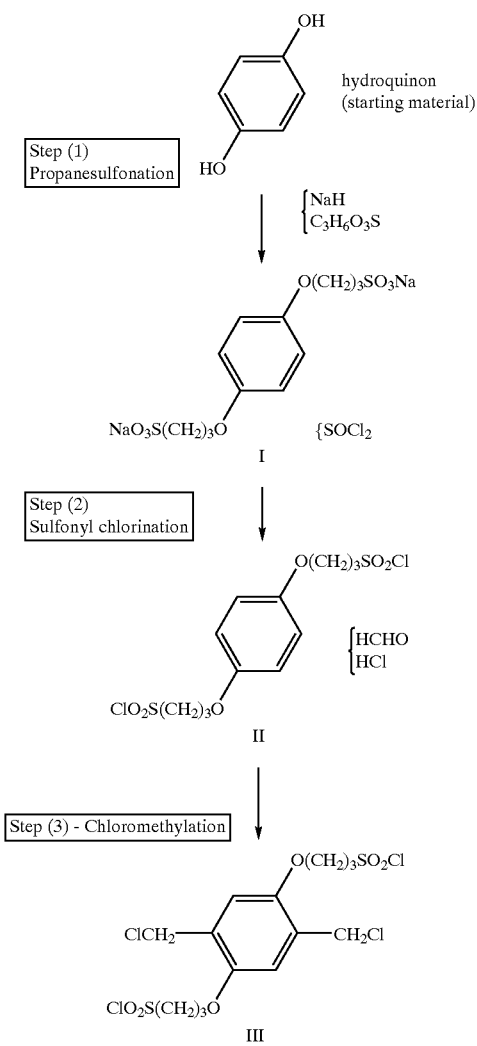

Step (1)—Alkanesulfonation

This step is to introduce an alkoxysulfonic acid group as a self-doping group to a benzene derivative or a naphthalene derivative having a hydroxyl group bonded to the aromatic ring thereof by alkanesulfonation of the hydroxyl group.

About 1 mol of hydroquinone (starting material) is dissolved in an adequate amount of N,N-dimethylformamide (DMF), and about 2 to 2.5 mol of sodium hydride is added to the solution, followed by stirring at ambient temperature. After hydrogen evolution is ceased, and a sodium alkoxide is formed, the reaction solution is heated to about 110 to 135° C., preferably about 130° C. About 2 mol of propanesulfonic acid is added to the solution dropwise, and the mixture is stirred for about 120 to 480 minutes, preferably about 300 minutes, at a temperature kept at about 130° C., followed by allowing the mixture to cool. Acetone is added thereto, and the stirring is continued. The solid thus precipitated is collected by filtration by suction, washed with acetone, and dried in vacuo to give crystals of a sodium benzene-2,5-dipropoxysulfonate (designated compound I).

Any benzene or naphthalene derivative having a hydroxyl group bonded to the aromatic nucleus can be used as a starting material. Such compounds include hydroquinones, phenols, and hydroxynaphthalenes. The number of a hydroxyl group is 1 or preferably 2. A starting compound with two hydroxyl groups provides a monomer with two self-doping groups which will provide a self-doped conductive polymer having higher conductivity than that obtained from a starting compound with one hydroxyl group.

The aromatic ring of the aromatic starting compound may have a substituent(s) other than a hydroxyl group unless the substituent gives adverse influences to polymerization, such as side reactions. Examples of substituents that may be bonded to the aromatic ring include an alkyl group, an alkoxy group, an alkyl ester group, a halogen atom, a nitro group, a cyano group, an amino group, a trihalomethyl group, and a phenyl group.

In addition to the benzene or naphthalene derivatives, other aromatic compounds having a hydroxyl group bonded to the aromatic ring thereof, such as polycyclic compounds (e.g., anthracene derivatives, polypyrene derivatives, polyazulene derivatives, and polyfluorene derivatives) and heterocyclic compounds having aromaticity and containing N, S or O as a hetero atom are expected to be applicable to the process of the present invention unless such problems as side reactions and reactivity arise.

The alkanesulfonic acid to be added to the hydroxyl group is not limited to propanesulfonic acid selected above. Note that the alkane moiety of the alkanesulfonic acid is desirably a straight chain having 2 to 12 carbon atoms. With only one carbon atom in the alkane moiety, the electron attraction by the sulfonic acid moiety reduces the electron density on the conductive polymer, resulting in a reduction of conductivity. Too many carbon atoms in the alkane moiety makes the side chain too bulky to allow polymer main chains to come into contact with each other or get close to each other. As a result, electron conduction would be hindered to reduce the conductivity.

Step (2)—Sulfonyl Halogenation

This step is to protect the self-doping group introduced in the step (1) by converting to an acid halide form (acid chloride in the example shown in scheme A) thereby to prevent a side reaction from occurring in the subsequent reactions.

About 1 mol of compound I is dissolved in an appropriate amount of DMF, and about 2 mol of thionyl chloride is added dropwise to the solution at ambient temperature. After stirring the mixture for at least about 60 minutes, preferably about 90 minutes, hexane and diethyl ether are added to the mixture in a total amount approximately equal to the amount of DMF. The mixture is stirred, followed by liquid-liquid separation. The upper organic layer is separated and evaporated under reduced pressure to remove the solvents to afford benzene-2,5-dipropoxysulfonyl chloride (designated compound II).

The step (2) is advantageous in that the halide moiety of the resulting compound completely suppresses side reactions in the subsequent reactions and is easily removable to restore the self-doping group (deprotection).

Step (3)—Chloromethylation

About 1000 ml of formaldehyde (37%) and about 700 ml of hydrochloric acid are sufficiently cooled in an ice bath while stirring, and hydrogen chloride gas is bubbled through the mixture until saturation. About 1 mol of compound II is dissolved in an appropriate amount of dioxane, and the solution is poured into the formaldehyde/hydrochloric acid mixture. The mixture is stirred at ambient temperature for about 180 to 300 minutes, preferably about 240 minutes, while bubbling hydrogen chloride gas. The precipitated white solid is collected by suction filtration and dried in vacuo to give crystals of 1,4-dichloro-p-xylene-2,5-dipropoxysulfonyl chloride (designated compound III).

Step (3) is a method called Blanc reaction, widely used as a chloromethylating means, by which a chloromethyl group as a polymerizable group is introduced to an aromatic ring to provide an aromatic monomer capable of producing a self-doped conductive polymer.

Synthesis of a self-doped conductive polymer by polymerizing the thus obtained aromatic monomer is then described. While the aromatic monomer of the present invention can be either homopolymerized or copolymerized with a copolymerizable monomer(s) to provide a self-doped conductive polymer, synthesis will be described taking homopolymerization for an instance.

There are various processes conceivable for polymerizing the aromatic monomer. In what follows, a process involving addition of a sulfonium salt and a process involving dehydrohalogenation are taken for an instance.

The process involving sulfonium salt addition, which is a known technique as disclosed, e.g., in JP-W-8-510489 (The term "JP-W" as used herein means an "international patent application published in the Japanese national proceeding"), will be explained by way of reaction scheme B.

Scheme B:

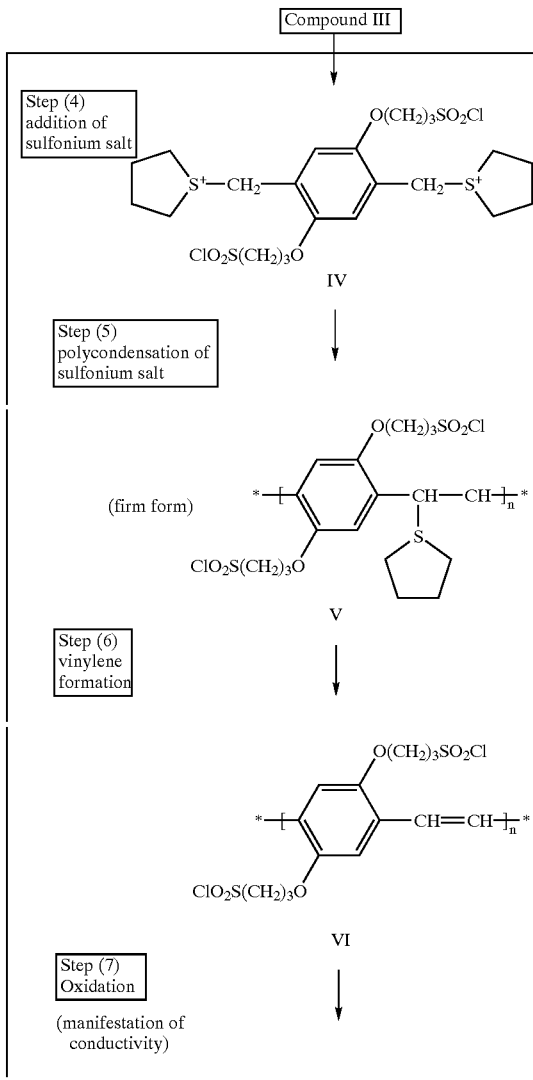

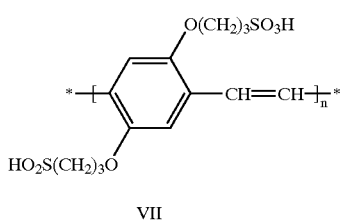

VII

Step (4)—Addition of Sulfonium Salt

This step is addition of a sulfonium salt to the chloromethyl group (polymerizable group) of the aromatic monomer. About 1 mol of compound III is dissolved in an appropriate amount of methanol, and about 2.5 mol of tetrahydrophiophene (THT) is added thereto, followed by heating with stirring in a nitrogen atmosphere. The mixture is refluxed at about 45 to 55° C., preferably about 50° C. or below, for about 12 to 36 hours, preferably about 24 hours. The solvent and any unreacted matter are removed by evaporation under reduced pressure at about 25 to 40° C., preferably about 30° C., to give a viscous substance. An appropriate amount of dehydrated acetone is added thereto, and the system is allowed to stand in a sealed container at about −5° C. or below for about 48 hours. The solid thus precipitated is collected by suction filtration and dried in vacuo to give crystals of 2,5-di(propoxysulfonyl chloride)-1,4-dimethylthiolane halide (designated compound IV).

The reagent to be used for sulfonium salt addition is not limited to THT. For example, dialkyl sulfides such as dimethyl sulfide and diethyl sulfide are also useful. It is desirable to select such a sulfonium salt that is easily releasable in the subsequent vacuum heating treatment at a temperature that does not influence the alkoxysulfonic acid moiety.

Step (5)—Polycondensation of Sulfonium Salt

This step is polycondensation of compound IV obtained in step (4). In about 500 ml of water is dissolved about 1 mol of compound IV, and the solution is stirred in an ice bath for about 60 to 180 minutes, preferably about 120 minutes, while deaerating by bubbling with nitrogen. To the solution is added dropwise about 1000 to 2000 ml of a 1 mol/l solution of sodium hydroxide, and the mixture is stirred in an ice bath for about 12 to 48 hours, preferably about 24 to 28 hours, while deaerating. The resulting viscous solution is put into a dialysis tube (cut-off molecular weight: 12,000 or greater), and the tube is sealed and immersed in distilled water. The dialyzate is concentrated by low-temperature vacuum distillation to yield poly(2,5-di(propoxysulfonyl chloride)-1,4-phenylene(α-S-thiolanyl)ethylene) (designated compound V).

The alkali solution used for polymerization reaction is not limited to the sodium hydroxide solution used above. For example, other alkali metal hydroxides, e.g., KOH, and alkaline earth metal hydroxides, e.g., $Ba(OH)_2$ and $Ca(OH)_2$, are useful as well. The cut-off molecular weight of the dialysis tube is subject to alteration according to the purpose.

Step (6)—Vinylene Formation

This step comprises vacuum heating treatment of compound V to release the sulfonium salt, thereby leaving a phenylene vinylene backbone (or a naphthylene vinylene backbone when the synthesis starts with a naphthylene derivative).

An aqueous solution of compound V is cast into film. The cast film is heated in vacuo at about 180 to 250° C., preferably about 200 to 220° C., for about 6 to 24 hours, preferably about 12 to 18 hours, whereby the sulfonium salt is released to form poly(1,4-phenylene vinylene-2,5-dipropoxysulfonyl chloride) (designated compound VI) in film form.

The form of compound VI includes not only film but powder, etc. The heat treating temperature in step (6) is subject to variation depending on the kinds of the alkoxy moiety and the sulfonium salt, the sample size, and the like.

Step (7)—Oxidation (Manifestation of Conductivity)

Compound VI obtained in step (6) is oxidized by immersion in an excess protonic acid (e.g., hydrochloric acid or sulfuric acid) to yield poly(1,4-phenylene vinylene-2,5-dipropoxysulfonic acid) as a final product. Step (7) is deprotection of the self-doping group that has been blocked (protected) in the foregoing reactions thereby to render compound VI conductive.

Self-doped PPVs synthesized by the above-described process usually have a molecular weight of 100,000 or more.

The process involving dehydrohalogenation of compound III will be described by referring to reaction scheme C. This process is also a known technique as disclosed, e.g., in JP-W-8-510483.

Scheme C:

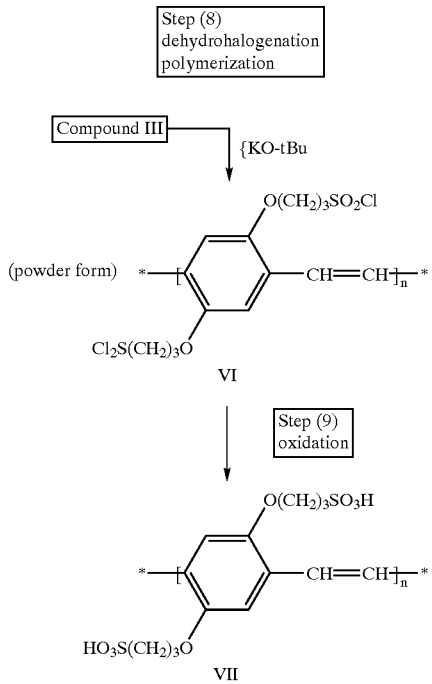

Step (8)—Dehydrohalogenation Polymerization

In an appropriate amount of tetrahydrofuran (THF) are dissolved about 1 mol of compound III, and the solution is stirred for about 10 to 60 minutes, preferably about 30 minutes, while deaerating by nitrogen bubbling. A THF solution containing 2 to 3 mol of potassium t-butoxide per mole of compound III as a polymerization initiator is added dropwise to the monomer solution while stirring and bubbling with nitrogen in an ice bath. After the dropwise addition, the reaction system is allowed to stand as such for about 12 to 24 hours. Excess methanol is added thereto, and the precipitated solid is collected by filtration by suction and dried in vacuo to give compound VI.

Step (9)—Oxidation

Compound VI is oxidized in the same manner as in step (7) described above to yield a self-doped conductive PPV as a powder. The resulting polymer usually has a molecular weight of 20,000 to 50,000.

A self-doped conductive polymer can be synthesized by either of the above-described processes or any other general-purpose polymerization methods. The polymerization process involving dehydrohalogenation is advantageous for obtaining polymers having lower molecular weights than those obtained by the process using a sulfonium salt.

As stated, the aromatic monomer (compound III) can be copolymerized with other copolymerizable monomers which are aromatic compounds or compounds capable of forming a pi-electron conjugated structure. For example, a binary copolymer represented by formula (2) (hereinafter referred to as a composite type PPV) can be produced by copolymerization.

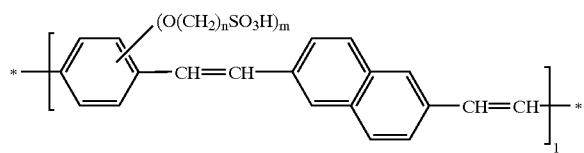

(2)

wherein l represents an integer of 10 to $10^4$; m represents 1 or 2; and n represents an integer of 2 to 12.

Compared with the above-described homopolymer, the composite type PPV of formula (2) exhibits better processability and, when left to stand in the air, undergoes smaller reduction in conductivity thereby maintaining a satisfactory conductivity over a longer period of time.

According to the present invention, aromatic monomers capable of providing self-doped conductive polymers in high yield are obtained. The aromatic monomers are capable of producing only self-doped conductive polymers of intended structure without undergoing side reactions during polymerization.

Since the process of producing the aromatic monomer starts with a benzene or naphthalene derivative having a hydroxyl group bonded, an alkoxysulfonic acid group (self-doping group) can be formed through a single step of alkanesulfonation of the hydroxyl group. This achieves reduction in number of steps required and improvement in yield. Further, a side reaction of the alkoxysulfonic acid group is prevented from occurring in the subsequent reactions (i.e., chloromethylation and polymerization) by blocking the acid group in the form of a sulfonyl halide. The blocking and deblocking can be effected through a minimized number of steps because the sulfonyl halide form is easily oxidized to restore the sulfonic acid form as a self-doping group.

Furthermore, the self-doped conductive polymer of the invention is extremely stable, possesses satisfactory processability, and retains satisfactory conductivity for an extended period of time.

EXAMPLES

Examples 1 and 2

In Example 1, an aromatic monomer of formula (1) in which m is 2 (the alkoxysulfonyl chloride groups are bonded to the same positions as shown in reaction schemes A to C), and n is 3 was homopolymerized according to the process of the present invention to produce a self-doped PPV having a molecular weight of 115,000.

In Example 2, the same aromatic monomer was copolymerized according to the process of the present invention to produce a self-doped composite type PPV represented by formula (2) having a molecular weight of 103,000.

The average molecular weight of the polymers was measured by gel-permeation chromatography using polyethylene glycol standards available from Wako Pure Chemical Industries, Ltd. The conductivity of the conductive polymers was measured with a resistance meter Low Rester GP, supplied by Mitsubishi Chemical Corp., with a four-point probe array according to JIS K7194. The results obtained are shown in FIG. 1. As can be seen from FIG. 1, while both the polymers exhibit satisfactory conductivity, the reduction in conductivity with time shown by the composite type PPV (copolymer) of Example 2 is apparently smaller than that shown by the PPV (homopolymer) of Example 1, revealing that introduction of a comonomer makes it possible to obtain satisfactory conductivity for an extended period of time.

Example 3

Butane sultone ($C_4H_8O_3S$) (produced by Tokyo Kasei Kogyo Co., Ltd.) is subjected to alkanesulfonation, sulfonylhalogenation, chloromethylation and conversion to sulfonium salt in the same manner as propane sulfone to synthesize a butane sultone self-doped PPV monomer represented by the following formula:

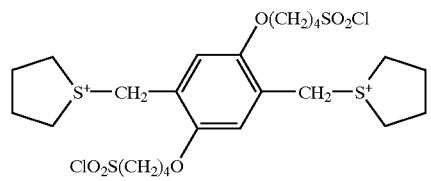

The butane sultone self-doped PPV monomer thus synthesized is then subjected to condensation polymerization and vinylation to obtain a butane sultone self-doped PPV polymer represented by the following chemical formula:

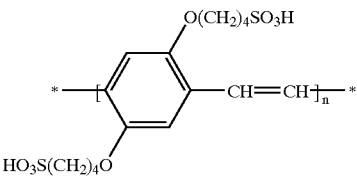

For the oxidation in Example 3, HCl was used.

The butane sultone self-doped PPV monomer of Example 3 is a product of homopolymerization of aromatic monomers represented by the aforementioned chemical formula (1) wherein m is 2 (connection position of self-doping group is the same as in Scheme. 1, 2 or 3) and n is 4.

Figure 2:
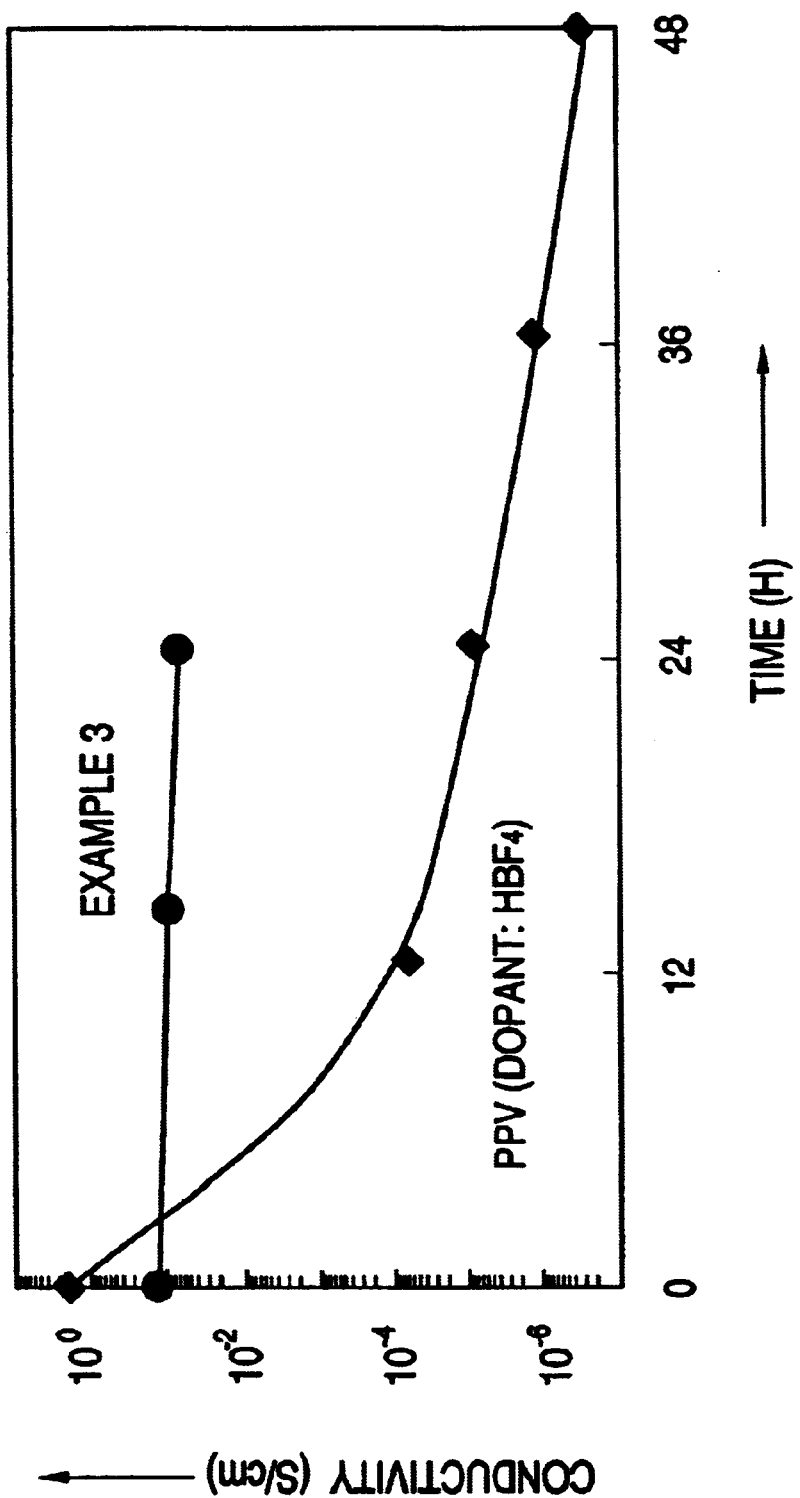
FIG. 2 is a graph showing the change of PPV of Example 3 and comparative PPV with time.

The measurements of conductivity of Example 3 are shown in FIG. 2.

As can be seen in FIG. 2, the butane sulfone self-doped PPV polymer of Example 3 exhibits a good conductivity and a conductivity change with time which is obviously smaller than that of the comparative PPV.

This application is based on Japanese Patent application JP 2001-182369, filed Jun. 15, 2001, the entire content of which is hereby incorporated by reference, the same as if set forth at length.

What is claimed is:

1. A process for producing an aromatic monomer for synthesizing a self-doped conductive polymer, the process comprising:

introducing an alkoxysulfonic acid group as a self-doping group to a benzene or naphthalene derivative having a hydroxyl group bonded to an aromatic ring thereof by alkanesulfonation of the hydroxyl group;

protecting the self-doping group by converting to an acid halide form by sulfonyl halogenation; and introducing two chloromethyl groups as polymerizable groups into the aromatic ring.

2. The process according to claim 1, wherein the benzene or naphthalene derivative has two hydroxyl groups bonded to the aromatic ring thereof.

3. The process according to claim 1, wherein an alkanesulfonic acid used for the alkanesulfonation has a straight-chain alkane moiety comprising 2 to 12 carbon atoms.

4. The process according to claim 1, wherein the sulfonyl halogenation is carried out by using thionyl chloride.

5. A monomer for synthesizing a self-doped conductive polymer prepared by the process according to claim 1.

6. A process for producing a self-doped conductive polymer by starting with an aromatic monomer prepared by the process according to claim 1, which comprises:

converting the chloromethyl group of the aromatic monomer into a sulfonium salt form;

polycondensing the sulfonium salt monomer to form an intermediate polymer;

releasing the sulfonium salt moiety from the intermediate polymer to form a phenylene vinylene backbone or a naphthylene vinylene backbone; and deprotecting the protected self-doping group by oxidation.

7. A process for producing a self-doped conductive polymer by starting with an aromatic monomer prepared by the process according to claim 1, which comprises:

dehydrohalogenation polymerization of the aromatic monomer at the polymerizable group to form a phenylene vinylene backbone or a naphthylene vinylene backbone; and deprotecting the protected self-doping group by oxidation.

8. A self-doped conductive polymer represented by the following formula:

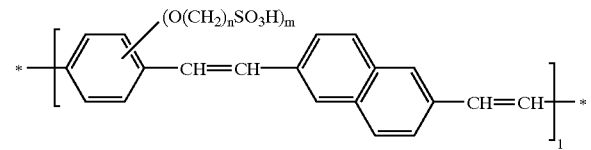

wherein l represents an integer of 10 to $10^4$; m represents 1 or 2; and n represents an integer of 2 to 12.

9. A process for synthesizing a self-doped conductive polymer represented by the following formula:

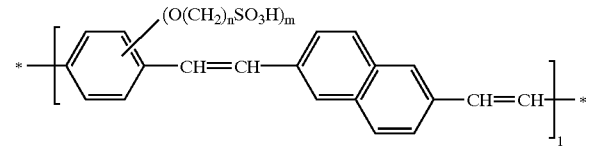

wherein l represents an integer of 10 to $10^4$; m represents 1 or 2; and n represents an integer of 2 to 12, the process comprising using an aromatic monomer prepared by the process according to claim 1.

* * * * *